United States Patent [19]

Gardano et al.

[11] Patent Number: 5,146,008
[45] Date of Patent: Sep. 8, 1992

[54] PROCESS FOR THE SYNTHESIS OF AROMATIC PHENYL SUBSTITUTED DIOLS

[75] Inventors: Andrea Gardano, Vercelli; Alfredo Coassolo, Novara; Francesco Casagrande, San Nazzaro Sesia; Marco Foà; Larry L. Chapoy, both of Novara, all of Italy

[73] Assignee: Himont italia S.r.l., Milan, Italy

[21] Appl. No.: 672,092

[22] Filed: Mar. 19, 1991

Related U.S. Application Data

[63] Continuation-in-part of Ser. No. 569,215, Aug. 16, 1990, abandoned, which is a continuation of Ser. No. 367,548, Jun. 16, 1989, abandoned.

[30] Foreign Application Priority Data

Jun. 16, 1988 [IT] Italy ........................... 20983 A/88

[51] Int. Cl.$^5$ .................................................. C07C 39/17
[52] U.S. Cl. ..................................... 568/743; 568/719; 568/731; 568/734
[58] Field of Search ............... 568/744, 731, 746, 747, 568/716, 743, 719, 731, 734

[56] References Cited

U.S. PATENT DOCUMENTS

| 4,160,113 | 7/1979 | Müller et al. | 568/744 |
| 4,798,911 | 1/1989 | Lentz et al. | 568/747 |

FOREIGN PATENT DOCUMENTS

| 0346913 | 12/1989 | European Pat. Off. | 568/743 |
| 1036445 | 3/1976 | Japan | 568/744 |
| 51-91215 | 8/1976 | Japan | 260/744 |
| 1091215 | 8/1976 | Japan | 568/747 |

*Primary Examiner*—Lone: Werren B.
*Attorney, Agent, or Firm*—Willian Brinks Olds Hofer Gilson & Lione

[57] ABSTRACT

A process for the synthesis of phenyl substituted aromatic diols, obtained by dehydrogenation of the corresponding substituted cyclohexyl derivatives in the presence of a palladium supported catalyst, said palladium supported catalyst being prepared by a process which comprises treating a palladium hydrolysis compound with reducing agents.

22 Claims, No Drawings

PROCESS FOR THE SYNTHESIS OF AROMATIC PHENYL SUBSTITUTED DIOLS

TECHNICAL FIELD

This is a continuation-in-part of pending U.S. application Ser. No. 07/569,215 filed August 16, 1990, now abandoned, which in turn was a continuation of now abandoned application U.S. Ser. No. 07/367,548 filed Jun. 16, 1989, both of which applications are hereby incorporated by reference.

The present invention relates to a process for the synthesis of phenyl substituted aromatic diols.

More particularly the present invention relates to a process for the preparation of phenyl substituted aromatic diols, starting from the corresponding substituted cyclohexyl derivatives, by catalytic dehydrogenation.

BACKGROUND ART

The aromatic diols obtained in accordance with this invention are important compounds for the preparation of polyesters and, in particular, of liquid crystalline polyesters when the two hydroxyl groups are in parallel or coaxial position. The use of phenyl hydroquinone in the synthesis of liquid crystalline polymers is described in U.S. Pat. No. 4,159,365, 4,360,658 and 4,600,765, whereas the use of phenyl biphenol is described in Italian patent application 22746 A/87.

Phenyl substituted aromatic diols can be prepared from the corresponding quinones by arylation with a diazonium salt of aniline (Journal of Organic Chemistry page 4071, 1977). Such a process generally presents considerable drawbacks from a practical point of view because the starting products can not always be easily found on the market. Moreover, aniline presents a potential hazard as a carcinogen.

Catalytic dehydrogenation is described in U.S. Pat. No. 4,798,911. In this patent, a catalyst composition is claimed, based on the combination of Pd and Cu, which is loaded on a carbon support. The catalyst is prepared by contacting a heat-treated carbon support with a Pd-containing compound and a Cu-containing compound in a solvent. The catalyst is calcinated prior to use under conditions effective to decompose the Pd- and Cu-containing compounds employed for catalyst preparation. In particular the dehydrogenation of cyclohexylhydroquinone is set forth in Table 3 with high conversion (88%) and high selectivity (90%). By comparison in the same Table, it is shown that a similar catalyst containing 5% Pd and no Cu on carbon gives 100% conversion but extremely low selectivity (4%). In Table 3 the results of Pd-Cu/Al$_2$O$_3$ and Pd-Cu/SiO$_2$ catalysts are also set forth. Conversion is however highly unsatisfactory.

DISCLOSURE OF THE INVENTION

Applicants have now found that phenyl substituted aromatic diols can be obtained with high yields and conversions by a dehydrogenation process of the corresponding cyclohexyl substituted derivatives, using a supported dehydrogenation catalyst.

Therefore the object of the present invention is a process for the synthesis of phenyl substituted aromatic diols comprising dehydrogenating products having the general formula:

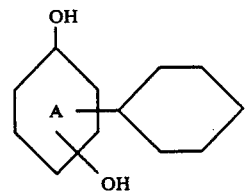

wherein A represents a single, double, triple or fused or condensed, C$_6$-C$_{18}$ aromatic radical, optionally substituted with groups which are inert under the reaction conditions, such as, for instance, C$_1$-C$_4$ alkyl radicals. The process is performed in the presence of a supported palladium catalyst, said supported palladium catalyst being prepared by a process which comprises treating a palladium hydrolysis compound with a reducing agent. Further objects will become evident in the description of the invention.

DETAILED DESCRIPTION OF THE INVENTION

In particular the dehydrogenation reaction takes place according to the following scheme:

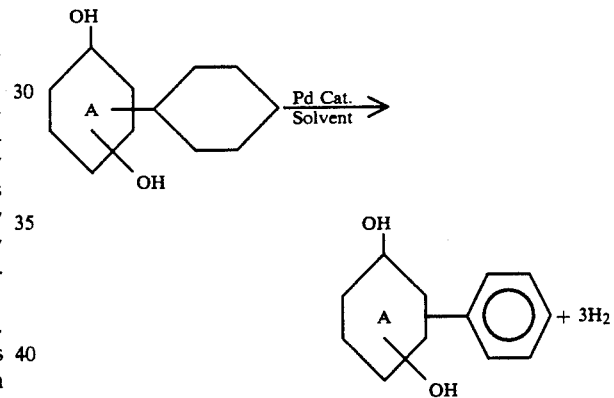

The cyclohexyl substituted aromatic diols having general formula (I) are known products, which can be obtained by alkylation of aromatic diols in the presence of acid catalysts, as described in G. A. Olah "Friedel-Crafts and Related Reactions" Vol. II, Part 1, 1964.

The products or compounds of formula (I), having the two hydroxyl groups in parallel or coaxial position are the preferred ones. Representative of such compounds are, cyclohexylhydroquinone, 3-cyclohexyl-4,4'-dihydroxydiphenyl, 1-cyclohexyl-2,6-dihydroxynaphthalene, 2-cyclohexyl-1,4-dihydroxynaphthalene and the like, The solvent medium used, besides having the property of dissolving the reagents under the reaction conditions, is endowed with a boiling point at atmospheric pressure, of at least 220° C. This allows one to reach the temperature desired for the dehydrogenation reaction; such temperature generally range from 220° to 350° C. Examples of solvents, utilizable in the present invention are: tetraethylene glycol dimethyl ether, diphenyl ether, diphenyl, polyethylene glycols having an average molecular weight ranging from 200 to 1500 such as, for instance, the ones marketed by R.O.L., an Oil and Lubricant Refinery, under trade-names Priowax 200, Priowax 400, Priowax 600 and so on.

The concentration of the reagent, or reactant, having formula (I) in the solvent medium is not critical. It can range within wide limits according to the nature of the reagent, to the kind of solvent, and in general to the selected operating parameters. More particularly such concentration may range from 5 to 75% calculated on the total weight of the solution.

The dehydrogenation reaction is preferably carried out at atmospheric pressure under a nitrogen flow to remove the developed hydrogen. Alternatively the reaction may also be carried out by operating under vacuum.

The catalyst used in the process of the present invention contains palladium and a suitable carrier. It is used with a molar ratio of reagent I/Pd ranging from 50 to 10,000, preferably from 50 to 2000.

Preferred carriers are extruded or granulated powdered activated carbons, activated aluminas and silicas, $TiO_2$, MgO and the like. Activated carbons, particularly suitable as carriers, are known products and have a specific surface ranging from 400 to 1200 $m^2/g$ and preferably from 600 to 1000 $m^2/g$. Activated aluminas and silicas are of microspheroidal type, in extruded form, or spheres. In the case of aluminas particularly good results were obtained when the specific surfaces were below 400 $M^2/g$, preferably between 10 and 350 $m^2/g$ and still more preferably between 30 and 300 $m^2/g$; in the case of silicas good results were obtained when the specific surfaces ranged from 100 to 800 $m^2/g$, preferably from 200 to 500 $m^2/g$. The pore volumes of activated aluminas range from 0.2 to 1.5 $cm^3/g$ and more preferably from 0.3 to 1.3 $cm^3/g$, whereas the pore volumes of silicas range from 0.5 to 2.5 $cm^3/g$ and more preferably from 1 to 2 $cm^3/g$. In the case of granulated titanium oxide or magnesium oxide the value of the specific surface is not critical; in the former case it may range from 10 to 300 $m^2/g$, in the latter from 10 to 500 $m^2/g$ The catalyst size is not particularly critical and essentially depends on the type of reactor to be used in the dehydrogenation reaction. Good results can be obtained both by powdered catalysts suspended in the reaction mass and by extruded, pasted, or granulated catalysts in tubular stream reactors.

The catalytic system is prepared according to the method described herein below which is one of the general methods described in the literature. An acid solution of a palladium halide like $PdCl_2$, or of sodium chloropalladite ($Na_2PdCl_4$) is added to an alkaline suspension of the powdered carrier. When the addition is over, the hydrolysis compound deposited on the carrier is turned into metal by treatment with a suitable reducing agent at a temperature ranging from 20° to 100° C. Reducing agents particularly suitable to this purpose are sodium hypophosphite and sodium formate. The solid product is recovered by filtration and rinsed with water at temperatures ranging from 20° to 100° C., until halide ions are removed, and optionally dried in an oven at 100°–120° C. over 10–15 hours. When a carrier of granulated, pasted or extruded type is used, a particularly advantageous method of preparation consists in letting the palladium compound absorb at the periphery, or surface, of the carrier granules; reduction, rinsing and drying, as described hereinbefore, will follow that operation.

According to a preferred embodiment of the process of the present invention, the catalytic system contains a small amount of alkalis so that, when it is dispersed in water, it supplies a pH over 7. Therefore it is better to treat the catalyst, before drying it, with a solution containing carbonates or bicarbonates of alkaline or alkaline-earth metals. The solution generally has a concentration ranging from 0.1 to 5% by weight calculated on metal ion.

The palladium content of the catalytic system is not critical, but it generally ranges from 0.1 to 10% by weight calculated on the dried solid. Preferably the catalyst, before the dehydrogenation reaction, is activated at 130°–150° C. for a period of time ranging about from 1 to 5 hours with hydrogen at atmospheric pressure.

According to a practical procedure, by operating for instance in a batch manner, the starting materials of general formula (I) and catalyst are added to the solvent in the above mentioned ratios, with a nitrogen flow, to make the removal of developed hydrogen easier. The reaction progress is checked by gas chromatography and the reaction is stopped preferably when the amount of cyclohexyl reactant is below 20% with respect to the starting amount of the reactant.

Reaction time range from 1 to 24 hours according to the selected operating parameters. When the reaction is over, the catalyst is recovered by decantation and filtration. The reaction product is recovered by known methods, for instance, by distilling the solvent or by diluting with water. The reaction raw product is subjected to the usual purification methods to obtain the phenyl substituted aromatic diol having the required purity. It is used, for instance, for the synthesis of polymers.

A few examples will be given hereinafter, by way of illustration but not of limitation, in order to better understand the present invention and to carry out the same. In the examples, elemental Pd is the reference when mention is made to concentrations and quantities of palladium. Unless otherwise indicated, the source of Pd was sodium chloropalladite.

EXAMPLE 1

60g of microspheroidal alumina marketed by CONDEA Company under trade-name "Puralox SCC A-30/180 Alumina", were dispersed with stirring in a solution consisting of 4g of sodium carbonate and 160ml of water. After stirring over 20 minutes, 20 ml of a hydrochloric acid solution having a pH of 0.8 and containing sodium chloropalladite (0.3g as elemental Pd) were added to the suspension in 30 minutes. Sodium ions were present in said solution, in such an amount that the atomic ratio Na/Pd was about 2.2. The sodium ions were present because of $Na_2PdCl_4$ and because NaCl was used to prepare the $Na_2PdCl_4$. When the addition was over, the slurry was heated, always under stirring, up to 85° C. and the temperature was kept at this value for 30 minutes; afterwards 0.4g of sodium formate, dissolved in 10cc of water, were added and the temperature was kept at 85° C. for further 10 minutes. The solid was recovered by filtration and rinsed with water at 50°–60° C. until disappearance of chloride ions. Afterwards it was dispersed in a solution containing 1g of sodium carbonate in 100ml of water and kept at rest overnight. After filtration the obtained cake was dried at 110° C. overnight. The catalyst, analyzed chemically, proved to contain 0.42% by weight of palladium.

EXAMPLE 2

6g of catalyst prepared according to the modalities described in Example 1, 10 g of cyclohexylhydroquinone and 30ml of tetraethylene glycol dimethyl ether were loaded, in nitrogen atmosphere, into a 100 ml flask equipped with a mechanical stirrer, thermometer, cooler and pipe for gas inlet. The temperature was brought to 270° C. and the mixture was kept at this temperature for 5 hours under a nitrogen flow. At the end of this period of time the gas chromatographic analysis showed a conversion of 97%. The phenylhydroquinone content in the raw product was 85%. The reaction raw product, after having been cooled to room temperature, was poured into water and extracted with ethyl ether. The ethereal solution was washed with a solution containing 10% of sodium metabisulphite and with $H_2O$. After drying with $Na_2SO_4$ and evaporation of the solvent a residue was obtained weighing 9.8 g. Such a residue was crystallized twice with toluene, thereby obtaining 7 g of practically pure phenylhydroquinone.

EXAMPLE 3

Example 1 was duplicated by using microspheroidal commercial alumina HARSHAW Al 3912 P. The catalyst, analyzed chemically, proved to contain 0.41% by weight of palladium.

EXAMPLE 4

6g of catalyst prepared according to the modalities described in Example 3, 10g of cyclohexyl hydroquinone and 30ml of tetraethylene glycol dimethyl ether were loaded into the same apparatus and under the same conditions of Example 2. The temperature was brought to 270° C. and the mixture was kept at this temperature for 5 hours under a nitrogen flow. Gas chromatographic analysis of the reaction mixture showed a conversion of 91% with a phenylhydroquinone content of 82%.

EXAMPLE 5

100g of microspheroidal alumina, Akzo type M, were calcined over 16 hours at 400° C. A part of the calcined alumina, 60g, was dispersed with stirring in a solution consisting of 8g of sodium carbonate and 250ml of water.

After stirring over 20 minutes, 0.6g of palladium (in the form of sodium chloropalladite), contained in 40 cc of a hydrochloric solution having a pH 0.8, was added over 30 minutes. Sodium ions were present in said solution, in such an amount that the atomic ratio Na/Pd was about 2.2. The sodium ions were present because of $Na_2PdCl_4$ and because NaCl was used to prepare the $Na_2PdCl_4$. After addition, the slurry was heated, always under stirring, up to 85° C. and, after 30 minutes, it was treated with 1.5 g of sodium formate dissolved in 15 ml of water and the temperature was kept at the same value for further 10 minutes. The subsequent procedures were the same as already described in Example 1.

Analysis: Pd=0.95%.

EXAMPLE 6

2 g of catalyst prepared according to the modalities described in Example 5, 10 g of cyclohexylhydroquinone and 30 g of biphenyl were loaded into the same apparatus and under the same conditions of Example 2. The temperature was brought to 250° C. and the mixture was kept at this temperature for 6 hours under a nitrogen flow.

Gas chromatographic analysis of the reaction mixture showed a conversion of 85% with a phenylhydroquinone content of 67%.

EXAMPLE 7

60 g of microspheroidal silica, marketed by Akzo Company as type F7, were dispersed, under stirring, in a solution consisting of 8 g of sodium carbonate in 350 ml of water. After stirring over 20 minutes, 0.6 g of palladium in a solution, as described in Example 5, was added. Then the temperature of the suspension was brought to 85° C. and kept at this value for 10 minutes; afterwards 1.5 g of sodium formate, dissolved in 15 ml of water, was added. After 10 minutes all the operations, described in Example 1, were carried out. The dipping of the product, after rinsing, was carried out in a solution of 2.5 g of sodium carbonate and 350 ml of water.

Analysis: Pd=0.96%

EXAMPLE 8

2 g of catalyst prepared according to the modalities described in Example 7, 10 g of cyclohexylhydroquinone and 30 ml of tetraethylene glycol dimethyl ether were loaded into the same apparatus and under the same conditions of Example 2. The temperature was brought to 260° C. and the mixture was kept at this temperature for 4 hours. Gas chromatographic analysis of the reaction mixture showed a conversion of 82%, with a phenylhydroquinone content of 61%.

EXAMPLE 9

50g of alumina spheres, having a diameter of 2.5 mm, marketed by HARSHAW Company as type Filtral SAS, were dipped in 400 ml of water for 1 hour. Afterwards they were drained. The drained carrier was introduced into a rotary baffle flask, then a hydrochloric acid solution having a pH of 2 was quickly poured onto said carrier; the hydrochloric solution contained 0.5 g of palladium (in the form of sodium chloropalladite) and sodium ions in such an amount that the atomic ratio Na/Pd was about 2.2. Palladium was allowed to absorb slowly under a flask rotation of 10–20 revolutions per minute. After decoloration of the solution 1 g of sodium formate dissolved in 50 cc of water was added and heated up to 70°–75° C. under slow rotation until the evolvement of gas stopped. Then the spheres were poured into a buckner and rinsed with water at 50°–60° C. until disappearance of chloride ions. At the end the spheres were dipped in a solution consisting of 4.6g of sodium carbonate and 130 ml of water and kept at rest overnight. After drainage the catalyst was dried at 110° C. overnight.

Analysis: Pd=0.93%.

EXAMPLE 10

2 g of catalyst prepared according to the modalities described in Example 9, 10 g of cyclohexylhydroquinone and 30 ml of tetraethylene glycol dimethyl ether were loaded into the same apparatus and under the same conditions of Example 2. The temperature was brought to 270° C. and the mixture was kept at this temperature for 3 hours under a nitrogen flow. Gas chromatographic analysis of the reaction mixture showed a conversion of 85% with a phenylhydroquinone content of 68%.

EXAMPLE 11

200 ml of distilled water were added slowly, in about 40 minutes and under stirring, to 200 ml of titanium tetraisopropylate (Ti(OC$_3$H$_7$)$_4$),in a 1000 ml beaker. At the end the mass was stirred for 11 hours. 6.7 g of sodium carbonate was then added, followed by stirring for an additional 20 minutes.

5.05 g of a solution containing about 10% by weight of palladium in the form of sodium chloropalladite and having pH 0.5, were diluted with water up to 40 ml. The pH was rectified by means of 10% HCl until a value of about 0.8 was reached. Afterwards the palladium solution thus obtained was added, in the course of 20 minutes, to the stirred suspension obtained by the hydrolysis of titanium isopropylate. When the addition was over the system was stirred for 30 minutes, then heated to 85° C., keeping the temperature at this value for 10 minutes. 1.25 g of sodium formate dissolved in 15 ml of water was slowly added. One then stirs for further 10 minutes, then one filtered and rinsed the solid until disappearance of chloride ions. The final product was dried at 120° C. overnight.

Analysis: Pd=1%.

EXAMPLE 12

4 g of catalyst prepared according to the modalities described in Example 11, 10 g of cyclohexylhydroquinone and 30 ml tetraethylene glycol dimethyl ether were loaded into the same apparatus and under the same conditions of Example 2. The temperature was brought to 270° C. and the mixture was kept at this temperature under a nitrogen flow for 5 hours. Gas chromatographic analysis of the reaction mixture showed a conversion of 59% with a phenylhydroquinone content of 43%.

EXAMPLE 13

50g of magnesium oxide (light magnesium oxide MP/18 produced by General Company for Industry of Magnesia, a joint stock company) were suspended in 400ml of water with stirring in a 1000 ml beaker. Afterwards 6.7 g. of sodium carbonate was added and subsequently, slowly in the course of 20 minutes, 5.05 g of a palladium solution prepared as described in Example 11 was added. At the end of the addition one proceeds in according to the modalities of Example 11.

Analysis: Pd=1%.

EXAMPLE 14

3 g of catalyst prepared according to the modalities described in Example 13, 10 g of cyclohexylhydroquinone and 30 ml of tetraethylene glycol dimethyl ether were loaded into the same apparatus and under the same conditions of Example 2, Then the temperature was brought to 260° C. and the mixture was kept at this temperature under a nitrogen flow for 5 hours. Gas chromatographic analysis of the reaction mixture showed a conversion of 79% with a phenylhydroquinone content of 64.5%.

EXAMPLE 15

610 g of coconut coal flakes having size of 40 mesh, marketed by PICA Company, as PICATAL A85 M, were rinsed carefully with water in order to remove the fine powder. When the rinsing was over, the coal was carefully drained and then alkalized with a solution obtained by dissolving 2.45 g of sodium bicarbonate in 700 cc of distilled water. The coal, after having been in contact with the solution for 40 minutes, was carefully drained and then poured into a rotary basket.

65.3g of a solution of sodium chloropalladite, containing about 10% by weight of palladium and having a pH of 0.6, was diluted up to 700 cc with distilled water and rectified to pH 2 by means of 10% HCl; afterwards 11 cc of H$_2$O$_2$ by 120 volumes were added. The palladium solution, 15 minutes after its preparation, was poured onto the coal at once, with the basket rotating slowly. After 40 minutes a solution of 57 g of sodium hypophosphite in 100 cc of water was poured into the basket. When the evolvement of hydrogen had ceased, the catalyst was taken away from the basket and rinsed by decantation until disappearance of chloride ions.

Analysis: Pd=1%.

EXAMPLE 16

2 g of catalyst prepared according to the modalities described in Example 15, 10 g of cyclohexylhydroquinone and 30 ml of tetraethylene glycol dimethyl ether were loaded in nitrogen atmosphere into a 100 ml flask equipped with mechanical stirrer, thermometer, cooler and pipe for gas inlet. The temperature was brought to 270° C. and the mixture was kept at this temperature under a nitrogen flow for 6 hours. Gas chromatographic analysis of the reaction mixture showed a conversion of 97% with a phenyl hydroquinone content of 84.4%.

EXAMPLE 17

1200 cm$^3$ of distilled water, 12 g of sodium carbonate previously dissolved in 40cm$^3$ of distilled water and 114 g of dried activated carbon having specific surface of about 950m$^2$/g were poured into a glass flask, equipped with a stirrer, and the mixture was vigorously stirred to disperse the carbon. Separately, about 80 cm$^3$ of an acid solution (pH about 0.5 for hydrochloric acid) of sodium chlorpalladite was prepared. This solution contained 6g of metallic palladium. This solution was dropped into the carbon suspension in about 50 minutes. After the addition the slurry was kept under stirring at room temperature for 30 minutes and then it was heated up to 80°-85° C.

In the meantime a solution was prepared by dissolving 12 g of sodium formate in 30cm$^3$ of distilled water. Said formate containing solution was added to the slurry in 3-4 portions to avoid excessive foaming; at the end the temperature was maintained at 80°-85° C. for 15 minutes and then the temperature was lowered at 60°-65° C. by introducing water at room temperature. The slurry was then filtered and the solid recovered was rinsed with distilled water until a weak reaction for halide ions of the rinsing water. The final product contained about 5% of palladium on a dry basis.

EXAMPLE 18

2 g of catalyst prepared according to the modalites described in Example 17, 20 g of cyclohexylhydroquinone and 150 ml of polyethylene glycol having mw 400 were loaded in a 250 ml 3-neck flask, fitted with a tube for the surface addition of gas, a mechanical stirrer, a thermometer and a condenser. Then the flask was heated and the temperature was maintained in the range 280°-290° C. During the course of the reaction, nitrogen was incorporated into the reaction atmosphere by subsurface addition thereof. After stirring the mixture for 10 hours at 280°-290° C., an aliquot of the reaction mixture was analyzed by gas chromatography and found to contain:

| | |
|---|---|
| phenylhydroquinone | 76% |
| cyclohexylhydroquinone | 6.5% |
| phenylphenols | 13.5% |
| diphenylhydroquinone | 2.5% |

EXAMPLE 19

400 cm$^3$ of distilled water, 47.5 g of dried activated carbon having specific surface of about 850m$^2$/g and 20 cm$^3$ of a 10% NaOH solution were poured into a glass flask, equipped with a stirrer, and the mixture was vigorously stirred to disperse the carbon. Separately, a 50 cm$^3$ of acid solution (pH lower than 1 for hydrochloric acid) of sodium chloropalladite was prepared. This solution contained 2.5 g of metallic palladium. Before use, said solution was treated with a 10% NaOH solution to a pH of about 4 and then rapidly poured into the alkaline suspension. The obtained slurry, under stirring, was treated with 0.8 g of sodium hypophosphite dissolved in 30 cm$^3$ of distilled water. At the end of the gas evolvement, the slurry was filtered and the recovered solid was rinsed with distilled water until a weak reaction for halide ions of the rinsing water. The final product contained about 5% of palladium on a dry basis.

EXAMPLE 20

The same procedure as in Example 18 was followed using the catalyst prepared according to Example 19. Comparable results as Example 18 were obtained.

We claim:

1. A process for the synthesis of phenyl substituted aromatic diols comprising dehydrogenating products having the general formula I:

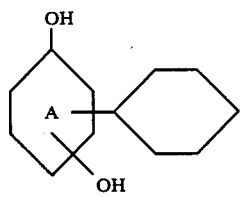

wherein A means a single, double, triple or fused C$_6$-C$_{18}$ aromatic radical, either unsubstituted or substituted with C$_1$-C$_4$ alkyl radicals, in a solvent medium in the presence of a supported palladium catalyst, wherein said supported palladium catalyst is prepared by a process comprising:
a) adding an acid solution of a palladium compound selected among palladium halide or palladite to an alkaline suspension of a carrier selected from the group consisting of activated carbons, activated aluminas, silicas, TiO$_2$ and MgO, thereby forming a slurry;
b) treating the slurry of a) at 20°–100° C. with sodium hypophosphite or sodium formate to turn said palladium compound into palladium metal;
c) recovering the solid product of the slurry of b) by filtration, rinsing said solid product with water at 20°–100° C. until halide ions are removed;
d) optionally, drying the solid at 100°–120° C. and wherein the dehydrogenation reaction is carried out at 220°–350° C., at atmospheric pressures under nitrogen flow or under vacuum.

2. A process according to claim 1 wherein the products having general formula (I) are products having the two hydroxyl groups in parallel or coaxial alignment.

3. A process according to claim 1 wherein the solvent medium is selected among products having the property of dissolving the reagents under the reaction conditions and a boiling point at atmospheric pressure of at least 200° C.

4. A process according to claim 1 wherein the catalyst is used in a molar ratio of produce (I)/Pd ranging from 50 to 10,000.

5. A process according to claim 1 wherein said activated carbon has a specific surface ranging from 400 to 1200 m$^2$/g.

6. A process according to claim 1 wherein said activated alumina has specific surfaces below 400 m$^2$/g.

7. A process according to claim 1 wherein said silica has specific surfaces ranging from 100 to 800 m$^2$/g.

8. A process according to claim 1 wherein said titanium oxide has a specific surface ranging from 10 to 300 m$^2$/g.

9. A process according to claim 1 wherein said catalyst contains an alkali, said alkali being obtained by treating the catalyst with a solution of carbonates or bicarbonates of alkaline or alkaline-earth metals.

10. A process according to claim 1 wherein the palladium compound is PdCl$_2$ or Na$_2$PdCl$_4$.

11. A process comprising (i) preparing a palladium catalyst by a process comprising:
a) adding an acid solution of a palladium compound selected among palladium halide or halopalladite to an alkaline suspension of a carrier selected from the group consisting of activated carbons, activated aluminas, silicas, TiO$_2$ and MgO, thereby forming a slurry;
b) treating the slurry of a) with sodium formate or sodium hypophosphite at 20°–100° C. to turn said palladium compound into palladium metal;
c) recovering the solid product of the slurry of b) by filtration, rinsing the solid with water at 20°–100° C. until halides are removed;
d) optionally, drying the solid of c) at 100°–120° C. and (ii) dehydrogenating at 220°–350° C. at atmospheric pressure under nitrogen flow or under vacuum, in a solvent medium, products having the formula I:

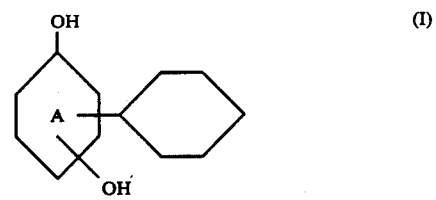

wherein A means a single, double, triple or fused C$_6$-C$_{18}$ aromatic radical, or products of formula I which are substituted with C$_1$-C$_4$ alkyl radicals, using the rinsed solid of c) or the dried solid of d) as a catalyst.

12. A process according to claim 11 wherein the products having general formula (I) are products having the two hydroxyl groups in parallel or coaxial alignment.

13. A process according to claim 11, wherein the products having general formula (I) are:
cyclohexylhydroquinone, 3-cyclohexyl-4,4'-dihydroxydiphenyl, 1-cyclohexyl-2,6-dihydroxynaphthaline and 2-cyclohexyl-1,4-dihydroxynaphthalene.

14. A process according to claim 11, wherein the solvent medium is selected among the products having the property of dissolving the reagents under the reaction conditions and a boiling point at atmospheric pressure of at least 220° C.

15. A process according to claim 3 wherein the solvent is tetraethylene glycol dimethyl ether, diphenyl ether, diphenyl or polyethylene glycols having an average molecular weight ranging from 200 to 1500.

16. A process according to claim 11 wherein the catalyst is used in a molar ratio of produce (I)/Pd ranging from 50 to 10,000.

17. A process according to claim 11 wherein said activated carbon has a specific surface ranging from 400 to 1200 $m^2/g$.

18. A process according to claim 11 wherein said activated alumina has specific surfaces below 400 $m^2/g$.

19. A process according to claim 11 wherein said silica has specific surfaces ranging from 100 to 800 $m^2/g$.

20. A process according to claim 11 wherein said titanium oxide has a specific surface ranging from 10 to 300 $m^2/g$.

21. A process according to claim 11 wherein said catalyst contains an alkali, said alkali being obtained by treating the catalyst with a solution of carbonates or bicarbonates of alkaline or alkaline-earth metals.

22. A process according to claim 11 wherein the palladium compound is $PdCl_2$ or $Na_2PdCl_4$.

* * * * *

UNITED STATES PATENT AND TRADEMARK OFFICE
CERTIFICATE OF CORRECTION

PATENT NO. : 5,146,008
DATED : September 8, 1992
INVENTOR(S) : Andrea Gardano et al.

It is certified that error appears in the above-identified patent and that said Letters Patent is hereby corrected as shown below:

On the title page, item [75]
line 4, insert the name -- Guido Petrini, Galliate, Italy -- between Marco Foa and Larry L. Chapoy.

Signed and Sealed this

Fourteenth Day of September, 1993

Attest:

BRUCE LEHMAN

Attesting Officer          Commissioner of Patents and Trademarks